US009788721B2

(12) United States Patent
Mittal et al.

(10) Patent No.: US 9,788,721 B2
(45) Date of Patent: Oct. 17, 2017

(54) LOW-POWER ACTIVITY MONITORING

(71) Applicant: BioBit Inc., Palo Alto, CA (US)

(72) Inventors: Rohit Mittal, Sunnyvale, CA (US); Neeraj Jhanji, Tokyo (JP)

(73) Assignee: BIOBIT, INC., Palo Alto, CA (US)

( * ) Notice: Subject to any disclaimer, the term of this patent is extended or adjusted under 35 U.S.C. 154(b) by 0 days.

(21) Appl. No.: 14/805,598

(22) Filed: Jul. 22, 2015

(65) Prior Publication Data

US 2016/0022141 A1    Jan. 28, 2016

Related U.S. Application Data

(60) Provisional application No. 61/999,268, filed on Jul. 22, 2014, provisional application No. 61/999,955, filed on Aug. 11, 2014.

(51) Int. Cl.

| | |
|---|---|
| A61B 5/00 | (2006.01) |
| H03M 1/12 | (2006.01) |
| G06F 7/58 | (2006.01) |
| H03M 1/46 | (2006.01) |
| A61B 5/11 | (2006.01) |
| H04M 1/725 | (2006.01) |

(52) U.S. Cl.
CPC ............ *A61B 5/0002* (2013.01); *G06F 7/582* (2013.01); *H03M 1/128* (2013.01); *A61B 5/0015* (2013.01); *A61B 5/1118* (2013.01); *H03M 1/1245* (2013.01); *H03M 1/468* (2013.01); *H04M 1/7253* (2013.01); *H04M 2250/12* (2013.01); *Y02B 60/50* (2013.01)

(58) Field of Classification Search
None
See application file for complete search history.

(56) References Cited

U.S. PATENT DOCUMENTS

| | | | |
|---|---|---|---|
| 5,836,982 A | 11/1998 | Muhlenberg et al. | |
| 7,592,808 B1 * | 9/2009 | King | G01R 33/56545 324/307 |
| 2002/0026122 A1 | 2/2002 | Lee et al. | |

(Continued)

OTHER PUBLICATIONS

Anna M. R. Dixon et al., "Compressed Sensing System Considerations for ECG and EMG Wireless Biosensors", IEEE Transactions on Biomedical Circuits and Systems, Apr. 2012, vol. 6, No. 2.

(Continued)

*Primary Examiner* — Joseph Feild
*Assistant Examiner* — John Mortell
(74) *Attorney, Agent, or Firm* — Mattingly & Malur, PC

(57) ABSTRACT

Some examples include a secure low-power sensor platform able to be used for activity monitoring or other purposes. For instance, a sensor system may sense sparse signals using compressed sensing. As one example, compressed sensing may be used to obtain sparse signals from analog sensor signals received from one or more sensors. The data obtained by compressed sensing may be sent subsequently to a computing device to reconstruct the sensor signal. Examples herein enable lower power usage, lower cost, and lower weight than conventional devices, while also enabling processing advantages, such as less overall data to process and lower data storage utilization.

22 Claims, 9 Drawing Sheets

(56) References Cited

U.S. PATENT DOCUMENTS

| | | | | |
|---|---|---|---|---|
| 2009/0222226 | A1* | 9/2009 | Baraniuk | H03M 13/11 |
| | | | | 702/66 |
| 2011/0080349 | A1* | 4/2011 | Holbein | G06F 1/3203 |
| | | | | 345/173 |
| 2011/0082377 | A1 | 4/2011 | Mahajan et al. | |
| 2012/0130645 | A1* | 5/2012 | Garudadri | A61B 5/0024 |
| | | | | 702/19 |
| 2013/0162457 | A1* | 6/2013 | Gangopadhyay | H03M 1/38 |
| | | | | 341/161 |
| 2015/0039260 | A1* | 2/2015 | Niskanen | G06K 9/6244 |
| | | | | 702/141 |

OTHER PUBLICATIONS

Pawan K. Baheti et al., "An ultra low power pulse oximeter sensor based on compressed sensing", 2009 Body Sensor Networks.

Emmanuel J. Candes et al., "An Introduction to Compressive Sampling", IEEE Signal Processing Magazine(21), Mar. 2008.

Wayne Talley et al., "Recent Developments for SAR and Sigma Delta ADCs", www.embedded.com/print/4013628, Jun. 27, 2005.

\* cited by examiner

LOW-POWER ACTIVITY MONITORING

CROSS-REFERENCES TO RELATED APPLICATIONS

This application claims the benefit of U.S. Provisional Patent Application No. 61/999,268, entitled "A secure always-on low-power activity monitoring system for fitness application", filed on Jul. 22, 2014, and U.S. Provisional Patent Application No. 61/999,955, entitled "A distributed compressed sensing framework for M2M communication", filed on Aug. 11, 2014, which are incorporated by reference herein in their entireties.

BACKGROUND

Activity monitoring has become popular in the fitness arena. People want to count the number of steps, decipher time spent or calories burnt on activities (e.g., walking, running, jumping, cycling), monitor their heart rates, and so forth. As several examples, mobile activity monitors may include various sensors, such as accelerometers, gyrometers, magnetometers (compasses), pressure sensor, GPS (global positioning system) receiver, and the like. However, the sensors, sensor blocks, and associated components included in activity monitors may consume substantial amounts of power, which can drain the batteries of mobile devices. For instance, the sensors may continually run at full speed, collecting large amounts of data. A sensor block may receive the data, and may often transmit the data wirelessly to another device. Further, in some examples, the sensor block may encrypt this data. Accordingly, conventional sensor blocks that receive and convey sensor signals may consume a substantial amount of power.

As an example, suppose an activity tracking device includes a sensor generating a signal in which the signal bandwidth includes frequencies up to 1 KHz. Thus, an analog-to-digital converter (ADC) may need to perform sampling of the analog signal at a rate of at least 2 KHz, which is the Nyquist rate of the highest frequency in the signal. In addition, a transmitter may need to transmit at that same rate, i.e., 2 KHz. Thus, when present, a transmitter may consume a large percentage of the total power consumed by the device. Further, other components of the device may also need to run at or above the Nyquist rate to match the operating speeds of the ADC and the transmitter.

In addition, a computing device that receives the data from the activity tracking device may need to store the large amount of sensor data and may further process the data. For example, the computing device may perform a substantial amount of data analysis and may generate a visual display of the data obtained by the sensor and sensor block of the device. Receiving and processing these large amounts of data may lead to high storage costs and may consume a significant amount of processing time and power.

Furthermore, ensuring security of the sensor data sent from the sensor block to the computing device may also drain considerable resources. For instance, sending data over wireless links may employ some mode of encryption, which may consume additional power and resources of the sensor block.

BRIEF DESCRIPTION OF THE DRAWINGS

The detailed description is set forth with reference to the accompanying figures. In the figures, the left-most digit(s) of a reference number identifies the figure in which the reference number first appears. The use of the same reference numbers in different figures indicates similar or identical items or features.

DETAILED DESCRIPTION

Figure 1:
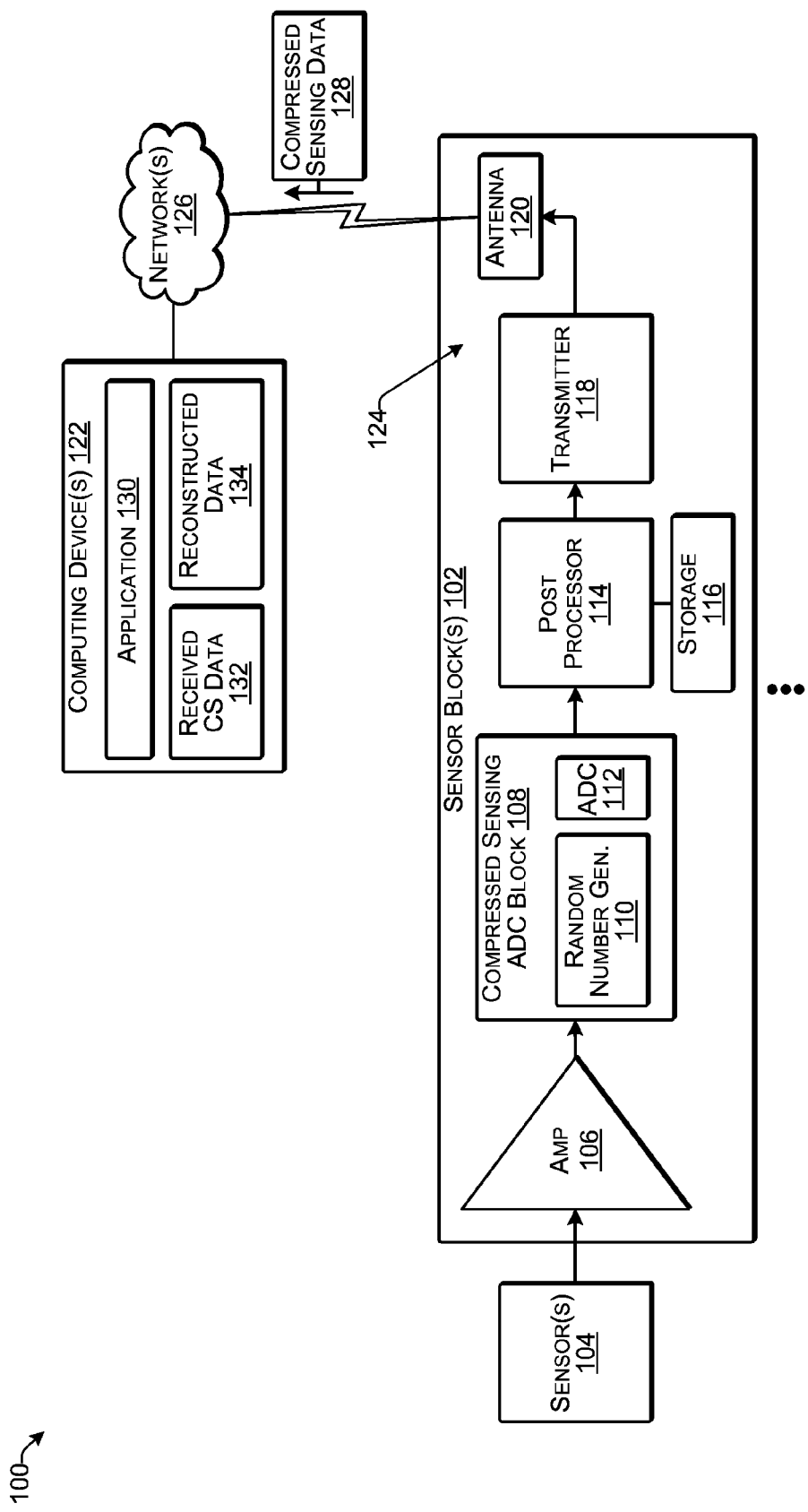
FIG. 1 illustrates an example compressed sensor system according to some implementations.

Some implementations herein include techniques and arrangements for a sensor platform able to be used for activity monitoring or other purposes. For instance, the system herein may sense sparse signals using compressed sensing (CS) and then process and reconstruct the data using a local or remote computing device or both. Further, implementations herein may enable secure and low-power sensor applications. As one example, compressed sensing may be used to obtain sparse signals from analog sensor signals received from one or more sensors, such as may be associated with an activity monitoring device. The data obtained by compressed sensing may be sent subsequently to a local and/or remote computing device to reconstruct the sensor signal. Examples herein enable lower power usage, lower cost, and lower weight than conventional devices, while also enabling processing advantages, such as less overall data to process and lower data storage utilization. In addition, some examples include an additional layer of security for data sent from a sensor block to the computing device.

A seminal paper on compressed sensing is "An Introduction to Compressive Sampling", Emmanuel J. Candes and Michael B. Wakin, IEEE Signal Processing Magazine, March 2008, which is incorporated by reference herein. Compressed sensing relies on two principles: sparsity, which pertains to the signals of interest, and incoherence, which pertains to the sensing modality. The principles of compressed sensing are based on efficient sensing or sampling protocols that capture a useful information content embedded in a sparse signal and condense this useful information into a small amount of data.

In some implementations, a platform for activity monitoring may include one or more sensor blocks and a connected computing device that receives sensed data from the sensor block. Each sensor block may include an amplifier, a compressed sensing analog-to-digital converter (ADC) block, a post processor, and a transmitter or other communication interface. The sensor block may receive a sensor signal from one or more sensors, may extract compressed sensing data from the sensor signal, and may transmit the compressed sensing data to a computing device that may store and reconstruct the compressed sensing data. In some examples, the compressed sensing data may be sent to and reconstructed by a local computing device, while in other examples, the compressed sensing data may be sent to and reconstructed by a server in the cloud and/or other connected computing device that performs the reconstruction of the compressed sensing data.

The compressed sensing ADC block may include a random number generator or pseudorandom number generator that causes the ADC to randomly sample an input signal received from the sensor, or from an amplifier that amplifies the signal from the sensor. In addition, the random number generator can also be used to generate a randomization matrix for securing the compressed sensing data sent from the sensor block to the computing device. Accordingly, the computing device that receives the compressed sensing data from the sensor block may use a corresponding randomization matrix to read the received compressed sensing data.

In some examples, the sensor block may include a storage that may receive the compressed sensing data from the ADC, and the compressed sensing data may be further subject to post processing prior to sending to the computing device. For instance, in the case that the compressed sensing data is transmitted wirelessly, the post processor may packetize the data, add transmission headers, timestamps, or the like.

In some examples, the storage may be one or more buffers that store the compressed sensing data temporarily while the post processing is performed. In other examples, the storage may be a larger memory or other suitable storage device able to store a substantial amount of compressed sensing data, and which may be duty cycled to further reduce power consumption of the sensor block. As one example, the storage may typically not consume power unless the compressed sensing block is adding sensed data to the storage.

The computing device that receives the compressed sensing data may include an application configured to reconstruct the compressed sensing data into a meaningful representation of the sensed signal. Furthermore, the computing device may perform predictive analytics on the sensed data, may store the reconstructed data, and make the reconstructed data accessible to users, third party tools, and so forth. In addition, the application on the computing device may include the ability to process compressed sensing data from multiple motion monitoring sensors or other activity monitoring sensors, and provide an accurate representation of the actual activity being performed. In some cases, the processing may be accomplished via signal processing algorithms ranging from simple subtraction to filtering and feature extraction.

In some examples, the sensor block may be implemented on an application-specific integrated circuit (ASIC) with merely a few external components, such as a sensor and an antenna. For instance, the sensor block may include a random number generator or pseudorandom number generator and a switched capacitor mixed signal block incorporated into the ASIC.

Furthermore, as mentioned above, the random number generator in the sensor block may also be used for securely transmitting the compressed sensing data. For instance, the sensor block may employ the random number generator to generate a multiplication matrix for compressed sensing, and the transmitter may use this matrix for securely transmitting the compressed sensing data. A computing device that receives the compressed sensing data may use the same random number generator and a decompression engine for decoding the received data.

Furthermore, some examples may use wavelet transforms to enable compressed sensing of sensor data received from activity sensors, or the like. As several examples, activity sensors may include accelerometers, gyrometers, a compass, proximity sensors, a pressure sensor, GPS receiver, or the like. Furthermore, implementations herein may use compressed sensing with frequency sparse signals for wearable devices, such as activity trackers, bracelets, smartwatches, ECG monitors, heartrate monitors, audio receiver, media player etc., as well as other wearable devices. For instance, any of the aforementioned sensors, such as an accelerometer, gyrometer, proximity sensor, magnetometer (compass), GPS receiver, pressure sensor, etc., may include an embedded compressed sensing front-end, such as the sensor block described herein.

For discussion purposes, some example implementations are described in the environment of compressive sensing of sensor signals associated with activity monitoring. However, implementations herein are not limited to the particular examples provided, and may be extended to other types of sensors, other usage environments, other system architectures, and so forth, as will be apparent to those of skill in the art in light of the disclosure herein.

FIG. 1 illustrates an example system 100 for compressive sensing according to some implementations. The system 100 includes one or more sensor blocks 102, each of which may receive a sensor signal from at least one sensor 104. The sensor 104 may include any suitable sensor. In some examples, the sensor may include one or more electrodes. Further, in some examples, the sensor 104 may be a micro-machined device, such as an accelerometer, gyroscope, pressure sensor, temperature sensor, compass, proximity sensor, or the like. Further, in some examples, the sensor 104 may be associated with an activity monitor or smartwatch, such as in the case of a motion sensor or a sensor for detecting a condition of the human body.

The sensor block 102 may further include an amplifier 106. For instance, the amplifier 106 may amplify the sensor signal received from the sensor 104. In some examples, the amplifier 106 may be omitted depending on the type and configuration of the sensor 104, the magnitude of the sensor signal, and so forth.

The sensor block 102 may further include a compressed sensing analog-to-digital conversion (ADC) block 108 for performing compressed sensing on the sensor signal received from the amplifier 106 and/or the sensor 104. For instance, the compressed sensing ADC block 108 may include a random number generator or pseudorandom number generator 110 (hereafter referred to as a "random number generator") and an ADC 112. The random number generator 110 may generate a random value or pseudorandom value using any of various techniques. The random values may be used for controlling sensor signal sampling performed by the ADC 112. The ADC 112 converts the sensor signal from an analog signal to a digital signal based on the random values, so as to generate a sparse random sampling of the sensor signal, which is output as compressed sensing data. Additional details of the compressed sensing ADC block 108 are discussed below with respect to FIG. 2.

The sensor block 102 may further include a post processor 114 and data storage 116. The storage 116 may receive the compressed sensing data from the ADC 112, and the compressed sensing data may be further subject to post processing by the post processor 114 prior to sending to the computing device. For instance, in the case that the compressed sensing data is transmitted wirelessly by a transmitter 118 and antenna 120, the post processor 114 may packetize the data, add transmission headers, timestamps, or the like. Further, in some examples, the post processor 114 may encrypt the compressed sensing data prior to sending the data to one or more computing devices 122.

In some examples, the storage 116 may merely be one more buffers that store the compressed sensing data temporarily while the post processing is performed. In other examples, the storage 116 may be a larger memory or other suitable storage device able to store a substantial amount of compressed sensing data. Additionally, in some instances, the storage 116 may be duty cycled to further reduce power consumption of the sensor block 102. As one example, the storage 116 may typically not consume power unless the compressed sensing ADC block 108 is adding compressed sensing data to the storage 116.

Further, in some cases, the post processor 114 and/or the transmitter 118 may normally be in an off condition and may periodically be wakened to send a threshold amount of stored compressed sensing data to the computing device 122. For instance, to reduce power, post processor 114 and/or transmitter 118 can queue the packets of compressed sensing data in the storage 116 and then transmit in burst mode instead of in a continual fashion. Thus, in some examples, at least one of the storage 116, the post-processor 114, or the communication interface 124 may cycle between an active state and a quiescent state based at least in part on the occurrence of sampling of the sensor signal by the compressed sensing ADC block 108 and/or based on the amount of compressed sensing data stored in the storage 116 reaching a threshold amount and/or based on user input or action. Accordingly, implementations herein are able to achieve significant power savings in comparison to conventional sensing blocks that continuously send sensor data to a computing device.

Further, in some examples, such as in the case that the computing device 122 is a local computing device, the computing device 122 may be similarly duty cycled, such as being wakened based on the receiving a burst of compressed sensing data being sent from a sensor block 102. As another alternative, the computing device 122 may wake periodically by itself or based on user input or action and poll a plurality of sensor blocks 102 for compressed sensing data, receive the compressed sensing data, perform processing or send the compressed sensing data to another computing device over the networks 126, and then return to a quiescent state.

Furthermore, while a transmitter 118 and antenna 120 are shown in the example of FIG. 1 as an example communication interface 124, in other examples, a different type of communication interface 124 may be used for conveying the compressed sensing data from the sensor block 102 to the computing device 122. Examples of other types of communication interfaces 124 may include hardwired connections, pluggable connections, optical communication interfaces, and so forth.

In some examples, the computing device 122 may be a local computing device that is local to the sensor block 102, and may be directly connected, such as by a wire, or may receive direct wireless communication, such as through BLUETOOTH® or other short range wireless communication technology. In other examples, as illustrated, the computing device 122 may be a local computing device or a remote computing device accessed over one or more networks 126. For instance, the computing device 122 may be a local computing device, such as a desktop or laptop computer, tablet, smartphone, smartwatch, or other computing device, accessed through a local area network. Alternatively, the computing device 122 may be a remote computing device, such as in the case of a cloud-based server, web server, or the like, accessed through the Internet or other suitable wide area network. Further, in some examples, there may be multiple computing devices 122, such as both a local computing device and a remote computing device. For example, the local computing device may receive compressed sensing data 128 from the sensor block, and may forward the compressed sensing data to a remote computing device, with or without performing any processing or reconstruction of the compressed sensing data.

The sensor block 102 may receive real life sensor data (such as xyz coordinates of gyroscope information) through an analog sensor signal and may convert this sensor signal into digital data in the compressed sensing ADC block 108. This raw compressed sensing data may be further processed by the post processor 114 where addition of packet headers, encryption, etc. may be accomplished. Subsequently the packetized data may be sent to the computing device 122 such as through the one or more networks 126 or directly. There may be any number of the sensor blocks 102 in communication with the computing device 122.

The one or more networks 126 can include any suitable network, including a wide area network, such as the Internet; a local area network, such as an intranet; a wireless network, such as a cellular network; a local wireless network, such as Wi-Fi; close-range wireless communications, such as BLUETOOTH®; a wired (for example fiber, coaxial or copper) network, such as Ethernet; or any other suitable network, or any combination thereof. Accordingly, the one or more networks 106 may include both wired and/or wireless communication technologies. Components used for such communication technologies can depend at least in part upon the type of network and/or the environment selected. Protocols for communicating over such networks are well known and will not be discussed herein in detail. Accordingly, the transmitter 118 or other communication interface 124 of the sensor block 102 may be configured for sending compressed sensing data 128 over the one or more networks 126 to the computing device 122.

The computing device 122 may include an application 130 that may receive the compressed sensing data 128 as received CS data 132. The computing device 122 may further execute the application 130 to reconstruct the compressed sensing data to obtain reconstructed data 134. For example, the application 130 may reconstruct the sparse signal in the received compressed sensing data 132 to obtain a representation of the sensor signal received from the sensor 104. There are many forms of reconstruction algorithms, some of which are heuristic (e.g., greedy algorithms), whereas the others are more linear (e.g., La minimization algorithm).

As one example, for CS reconstruction models using constrained L1 minimization, larger coefficients are penalized heavily in the L1 norm. Some examples may employ a weighted formulation of L1 minimization designed to more democratically penalize nonzero coefficients. An iterative algorithm may be used for constructing the appropriate weights. Each iteration may solve one L1 minimization problem by finding the local minimum of a concave penalty function that more closely resembles the L0 norm. An additional parameter, usually to avoid any sharp transitions in the penalty function curve, is introduced into the iterative equation to ensure stability and so that a zero estimate in one iteration does not necessarily lead to a zero estimate in the next iteration. This technique essentially involves using the current solution for computing the weights to be used in the next iteration.

In some examples, the amplifier 106 may be implemented as a switched capacitor amplifier with a chopper or other means of mitigating 1/f noise. For instance, the amplifier 106 may be coupled to various electrodes as the sensor(s) 104 used to measure electrical data directly from a human patient. In other examples, the amplifier 106 may be omitted, such as the case that the sensor signal from the sensor 104 has sufficient magnitude to be detected by the compressed sensing ADC block 108. In some cases, the compressed sensing ADC block 108 may include a switched capacitor multiplier as the ADC 112 where the coefficients are multiplied by an LFSR (linear feedback shift register) that generates the random numbers. Additional details regarding the compressed sensing ADC block 108 are discussed below with respect to FIG. 2.

The post processor 114 may be implemented as a programmable state machine, microprocessor, or the like, that may be configurable for various standards, communication protocols, and security requirements. In addition, the storage 116 may be any suitable type of memory, storage device, or other computer-readable media, some examples of which are discussed below. As one example, the transmitter 118 may include an ultra-low-power switched-capacitor class C amplifier. Consequently, in some cases, the sensor block 102 may be implemented with a complementary metal-oxide semiconductor (CMOS) ASIC and a few external components such as the antenna 120 and the sensor 104, such as a pair of electrodes or other suitable sensor.

By not having to store a large amount of data (unlike in the case of Nyquist sampling), and then discarding this data, implementations of compressed sensing herein are able to conserve valuable power. For instance, compressed sensing may employ knowledge of signal sparsity. The compressed sensing ADC block 108 may use a randomization matrix to mix with the input signal received from the amplifier 106. This will also serve to spread the frequency content of the signal and prevent eavesdropping, much like with spread spectrum communication.

By utilizing compressed sensing ADC block 108, the sensor system 100 may use substantially less power than conventional sensing techniques. The compressed sensing ADC block 108 operates by relying upon an inherent sparsity of an input signal received from the sensor 104 and the amplifier 106, and without prior knowledge of the input signal, for sampling of the input signal below the Nyquist rate to reduce power consumption. The sampling rate of both the compressed sensing ADC block 108 and the transmitter 118 is reduced by a compression factor when compared to a conventional sensor block. This leads to a direct savings in power. Post processor 114 may also perform post processing operations on less data in sensor block 102 and at a slower rate than in conventional sensor blocks, leading to further power savings. As one example, the compressed sensing ADC block 108 herein may utilize a compression rate of 8×-16×, which will lead to a similar decrease in power consumption, e.g., an order of magnitude, for the sensor block 102 as compared to conventional sensor blocks. To further reduce power it is possible to queue up the compressed sensor data in storage 116 and then only send bursts of the data.

Compressed sensing is based on the principle that, through optimization, the sparsity of a signal can be exploited to recover it from far fewer samples than required by the Shannon-Nyquist sampling theorem. There are two conditions under which recovery is possible. The first one is sparsity, which requires the signal to be sparse in some domain. The second one is incoherence, which is applied through the isometric property, which is sufficient for sparse signals. Compressed sensing typically starts with taking a weighted linear combination of samples in a basis different from the basis in which the signal is known to be sparse. The number of these samples can be small and still contain nearly all the useful information. Portions of the article "An Introduction to Compressive Sampling," Emmanuel J. Candes and Michael B. Wakin, IEEE Signal Processing Magazine, March 2008, which is incorporated by reference herein, are set forth below to provide additional background information on compressed sensing processing techniques.

Conventional approaches to sampling signals or images follow Shannon's celebrated theorem: the sampling rate must be at least twice the maximum frequency present in the signal (the so-called Nyquist rate). In fact, this principle underlies nearly all signal acquisition protocols used in consumer audio and visual electronics, medical imaging devices, radio receivers, and so on. (For some signals, such as images that are not naturally bandlimited, the sampling rate is dictated not by the Shannon theorem, but by the desired temporal or spatial resolution. However, it is common in such systems to use an antialiasing low-pass filter to band limit the signal before sampling, and so the Shannon theorem plays an implicit role.) In the field of data conversion, for example, standard analog-to-digital converter (ADC) technology implements the usual quantized Shannon representation: the signal is uniformly sampled at or above the Nyquist rate. (IEEE Signal Processing Magazine, March 2008, page 21).

CS theory asserts that one can recover certain signals and images from far fewer samples or measurements than traditional methods use. To make this possible, CS relies on two principles: sparsity, which pertains to the signals of interest, and incoherence, which pertains to the sensing modality.

Sparsity expresses the idea that the "information rate" of a continuous time signal may be much smaller than suggested by its bandwidth, or that a discrete-time signal depends on a number of degrees of freedom, which is comparably much smaller than its (finite) length. More precisely, CS exploits the fact that many natural signals are sparse or compressible in the sense that they have concise representations when expressed in the proper basis v.

Incoherence extends the duality between time and frequency and expresses the idea that objects having a sparse representation in w must be spread out in the domain in which they are acquired, just as a Dirac or a spike in the time domain is spread out in the frequency domain. Put differently, incoherence says that unlike the signal of interest, the sampling/sensing waveforms have an extremely dense representation in ψ.

The crucial observation is that one can design efficient sensing or sampling protocols that capture the useful information content embedded in a sparse signal and condense it into a small amount of data. These protocols are nonadaptive and simply require correlating the signal with a small number of fixed waveforms that are incoherent with the sparsifying basis. What is most remarkable about these sampling protocols is that they allow a sensor to very efficiently capture the information in a sparse signal without trying to comprehend that signal. Further, there is a way to use numerical optimization to reconstruct the full-length signal from the small amount of collected data. In other words, CS is a very simple and efficient signal acquisition protocol which samples—in a signal independent fashion—at a low rate and later uses computational power for reconstruction from what appears to be an incomplete set of measurements. (IEEE Signal Processing Magazine, March 2008, page 22).

Many natural signals have concise representations when expressed in a convenient basis. Consider, for example, an image [ ] and its wavelet transform [ ]. Although nearly all the image pixels have nonzero values, the wavelet coefficients offer a concise summary: most coefficients are small and the relatively few large coefficients capture most of the information . . . . In plain terms, one can "throw away" a large fraction of the coefficients without much loss.

This principle is, of course, what underlies most modern lossy coders such as JPEG-2000 and many others, since a simple method for data compression would be to compute x from f and then (adaptively) encode the locations and values of the S significant coefficients. Such a process requires knowledge of all the n coefficients x, as the locations of the significant pieces of information may not be known in advance (they are signal dependent) . . . . More generally, sparsity is a fundamental modeling tool, which permits efficient fundamental signal processing; e.g., accurate statistical estimation and classification, efficient data compression, and so on. [A] more surprising and far-reaching implication, however, . . . is that sparsity has significant bearings on the acquisition process itself. Sparsity determines how efficiently one can acquire signals nonadaptively. (IEEE Signal Processing Magazine, March 2008, page 23).

In plain English, the Coherence measures the largest correlation between any two elements of the sensing basis $\Phi$ and the representation basis $\psi$. If $\Phi$ and $\psi$ contain correlated elements, the coherence is large. Otherwise, it is small . . . . CS is mainly concerned with low coherence pairs. (IEEE Signal Processing Magazine, March 2008, page 23).

1) The role of the coherence is completely transparent; the smaller the coherence, the fewer samples are needed, hence [the] emphasis on low coherence systems in the previous section.

2) One suffers no information loss by measuring just about any set of m coefficients, which may be far, less than the signal size apparently demands. If $\mu(\Phi, \psi)$ is equal or close to one, then on the order of S log n samples suffice instead of n.

3) The signal f can be exactly recovered from [a] condensed data set by minimizing a convex functional which does not assume any knowledge about the number of nonzero coordinates of x, their locations, or their amplitudes which we assume are all completely unknown a priori. We just run the algorithm and if the signal happens to be sufficiently sparse, exact recovery occurs.

The theorem indeed suggests a very concrete acquisition protocol: sample nonadaptively in an incoherent domain and invoke linear programming after the acquisition step. Following this protocol would essentially acquire the signal in a compressed form. All that is needed is a decoder to "decompress" this data; this is the role of L1 minimization. (IEEE Signal Processing Magazine, March 2008, page 24).

[Some examples show] that a number of samples just about 4× the sparsity level suffices. Many researchers have reported on similar empirical successes. There is de facto a known four-to-one practical rule, which says that for exact recovery, one needs about four incoherent samples per unknown nonzero term. (IEEE Signal Processing Magazine March 2008, page 26).

Data acquisition typically works as follows: massive amounts of data are collected only to be—in large part—discarded at the compression stage to facilitate storage and transmission. In the language of this article, one acquires a high-resolution pixel array f, computes the complete set of transform coefficients, encode the largest coefficients and discard all the others, essentially ending up with fS. This process of massive data acquisition followed by compression is extremely wasteful (one can think about a digital camera which has millions of imaging sensors, the pixels, but eventually encodes the picture in just a few hundred kilobytes).

CS operates very differently, and performs as "if it were possible to directly acquire just the important information about the object of interest." By taking about O(S log(n/S)) random projections as in "Random Sensing," one has enough information to reconstruct the signal with accuracy at least as good as that provided by fS, the best S-term approximation—the best compressed representation—of the object. In other words, CS measurement protocols essentially translate analog data into an already compressed digital form so that one can—at least in principle—obtain super-resolved signals from just a few sensors. All that is needed after the acquisition step is to "decompress" the measured data.

The fact that a compressible signal can be captured efficiently using a number of incoherent measurements that is proportional to its information level S<<n has implications that are far reaching and concern a number of possible applications. (IEEE Signal Processing Magazine March 2008, page 28).

The compressed sensing ADC block 108 may rely on the inherent sparsity and incoherence of an input signal received from the sensor 104 and/or the amplifier 106, without prior knowledge of the input signal, for sampling of the input signal below the Nyquist rate. Thus, by sampling below the Nyquist rate, the compressed sensing ADC block 108 enables the sensor block 102 to reduce the overall power consumed. For instance, as discussed additionally below with respect to FIG. 2, the compressed sensing ADC block 108 may include an analog-to-digital conversion block including a circuit to take random samples of a sensor signal and output compressed sensing data comprising the random samples.

In some examples, the system 100 may be used in collecting and managing "big data". Big data may include three components: velocity, volume, and value. For instance, one computing device 122 may be local and may communicate with another computing device 122 in the cloud that may receive the compressed sensing data in the raw form for processing. Thus, in some examples, the compressed sensing data may be processed by a cloud computing device and not a local computing device. Thus, in this example, the application 130 may be executed on the cloud computing device. Because a local computing device does not perform the data reconstruction and processing, the local computing device may also be optimized for low power consumption. Further, using compressed sensing may lower the storage cost for the collected data by as much as 10 to 20 times.

The sensor block 102 may employ a randomization matrix to mix with the input sensor signal. This randomization matrix may be used on the backend by the computing device 122 as well for decompression. Accordingly, there may be a synchronization mechanism between the sensor block 102 and the "authorized" backend, i.e., the computing device 122. There are many ways of synchronization that may be employed by the systems herein, including but not limited to header information, information exchange during pairing, or the like. An unauthorized backend computing device will not be able to decipher the compressed data.

Figure 2:
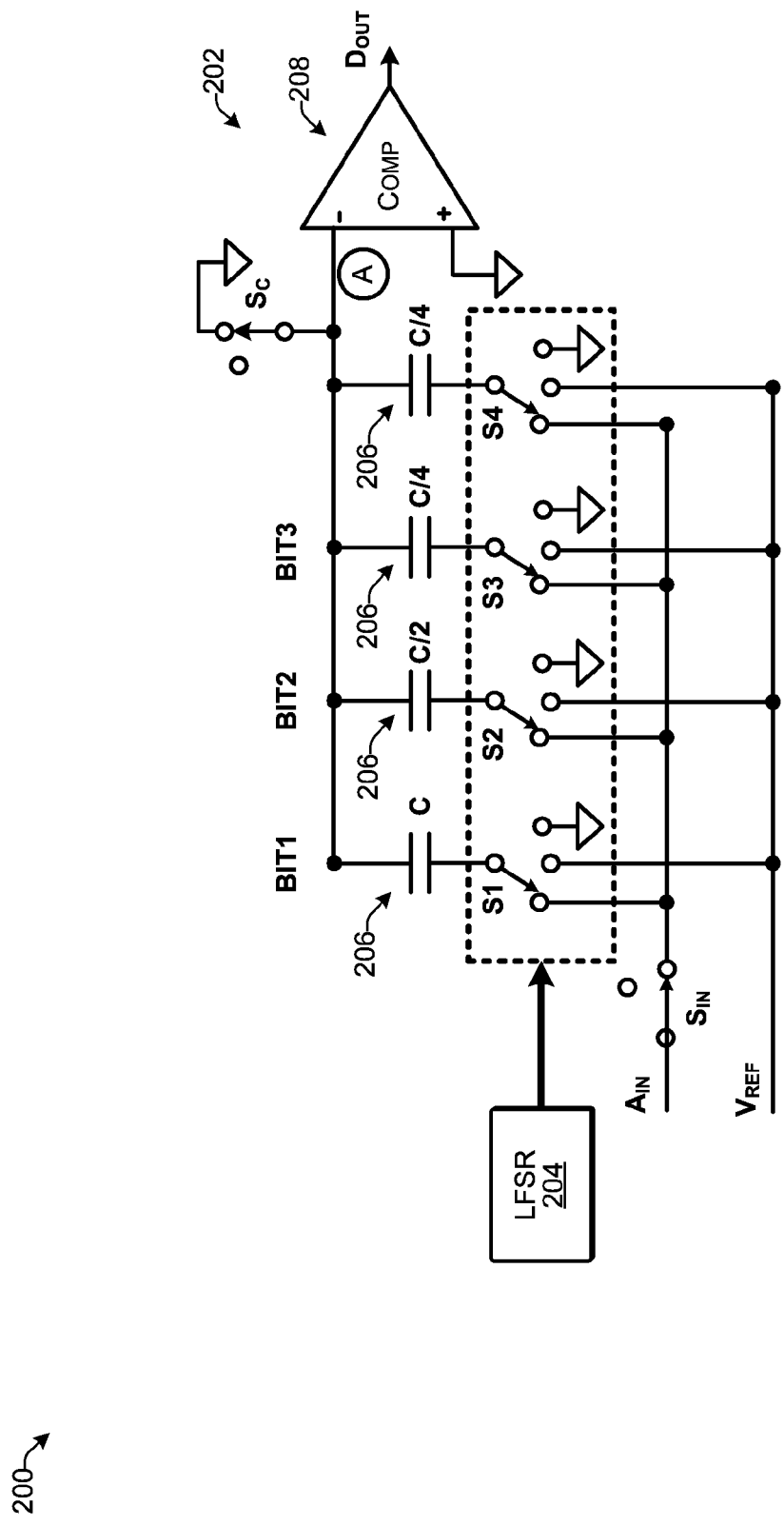
FIG. 2 illustrates an example of a circuit that may be included in the compressed sensing ADC block for performing the compressed sensing according to some implementations.

FIG. 2 illustrates one example of a circuit 200 that may be included in the compressed sensing ADC block 108 for performing the compressed sensing according to some implementations. In this example, the circuit 200 includes an SCDAC (switched capacitor digital-to-analog converter) 202 which may correspond at least in part to the ADC 112 discussed above with respect to FIG. 1. The circuit 200 further includes an LFSR (linear feedback shift register) 204, which may correspond at least in part to the random number generator 110 discussed above with respect to FIG. 1.

The SCDAC 202 includes a series of binary weighted capacitors 206 with their top plates connected to each other and also connected to the inverting input of a comparator 208. The SCDAC 202 further includes four switches S1, S2, S3, and S4, each of which is in line with a bottom plate of a respective one of the capacitors 206. The SCDAC 202 further includes an analog input line $A_{IN}$, an input switch $S_{IN}$, a reference voltage line $V_{REF}$, a comparator switch $S_C$, and an ammeter A.

In some examples, the weighting of each capacitor 206 may be one half the value of its neighbor, as illustrated, in order to prevent improper bit decisions made by the comparator 208. The bottom plate of each capacitor 206 is tied to a respective single-pole, triple-throw switch S1-S4. Each switch S1-S4 connects the individual capacitor 206 to either the voltage reference $V_{REF}$ or ground, depending on whether the respective bit is turned "ON" or "OFF", or to $A_N$ during a sensor signal sampling mode. The function of the comparator 208 is to swing high, if excess charge remains across the SCDAC array after each capacitor 206 is tested, or swing low if no charge is remaining. The input switch $S_{IN}$ between the analog input and the switches S1-S4 controls the sampling and conversion modes of the SCDAC 202.

In addition, the LFSR 204 may include a shift register whose input bit is a linear function of its previous state. As one example, the LFSR 204 may include a shift register whose input bit is driven by the XOR of some bits of the overall shift register value. Because the operation of the register may be deterministic, the stream of values produced by the register is completely determined by its current (or previous) state. Likewise, because the register has a finite number of possible states, it must eventually enter a repeating cycle. However, an LFSR 204 with a well-chosen feedback function can produce a sequence of bits which appears random and which has a very long cycle. Accordingly, the LFSR 204 in this example may serve as a pseudorandom number generator to generate random numbers. Thus, the LFSR 204 may be used to randomly change the bit values of switches S1-S4 in the SCDAC 202. The switches S1-S4 may be configured in one position or another other randomly. The output $D_{OUT}$ is a multiplication of the input signal $A_{IN}$ and the reference voltage $V_{REF}$ or ground based on positions of the switches S1-S4. Any suitable type of LFSR 204 may be used. Further, in other examples, a different type of randomness generator and/or a different type of ADC may be used, with the foregoing be merely one example for discussion purposes. To illustrate, there are many other ways of implementing the compressed sensing ADC block 108, some of which may use an ADC directly, while others may use an analog multiplier and then an ADC. However, in any implementation, the compression and security techniques discussed herein may still be accomplished.

Figure 3:
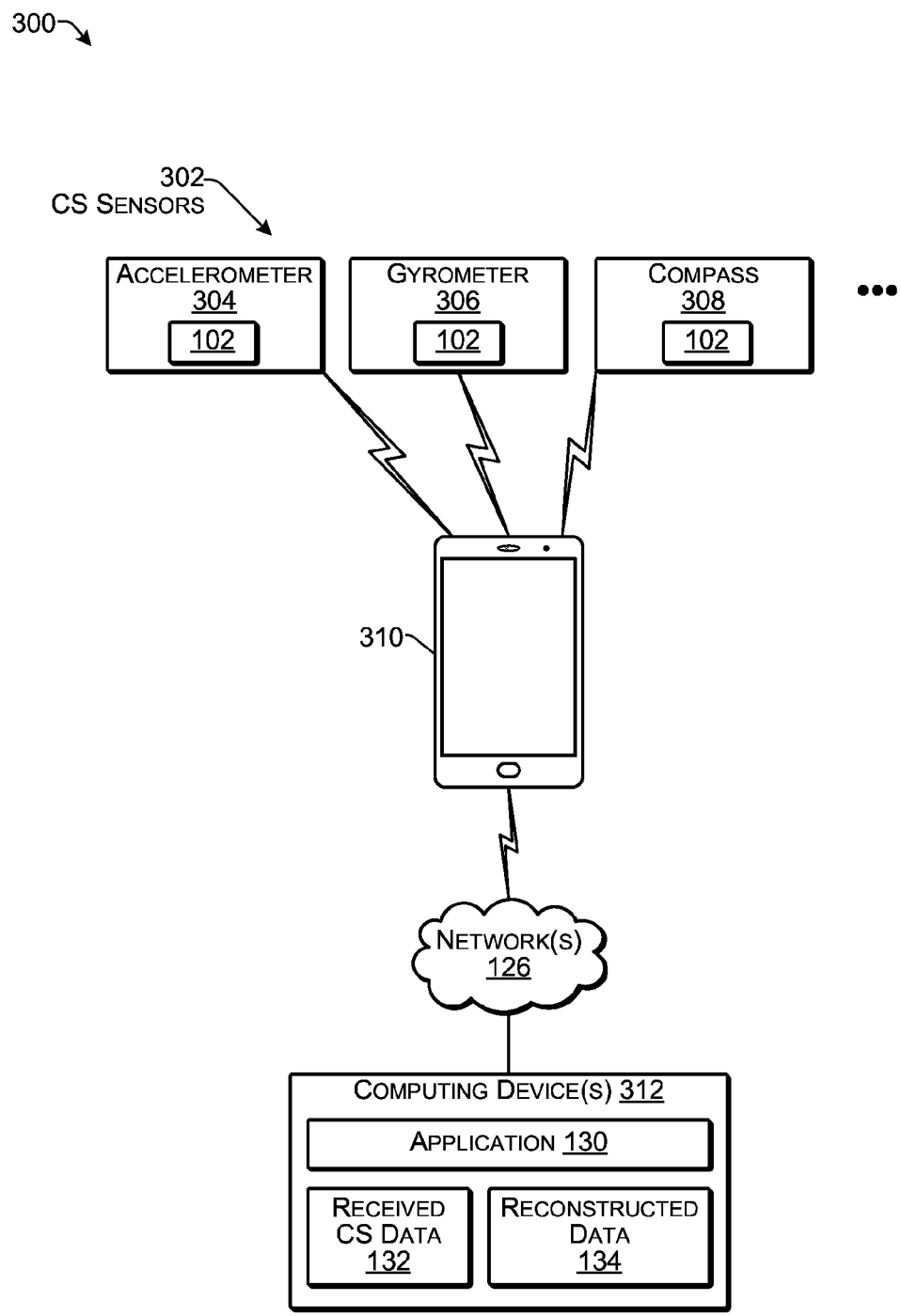
FIG. 3 illustrates an example system including a plurality of compressive sensing sensors, such as motion sensors or the like, according to some implementations.

FIG. 3 illustrates an example system 300 including a plurality of compressive sensing sensors 302, such as motion sensors or the like, according to some implementations. In this example, the plurality of compressive sensing sensors 302 include an accelerometer 304, a gyrometer 306, and compass 308, although other types of sensors may also be included. In this example, each of the compressive sensing sensors 302 may include a sensor block 102 as discussed above.

The compressive sensing sensors 302 may send compressed sensing data to a local computing device 310, which in this example is illustrated as a smartphone, smartwatch or other mobile device, but which may be any other suitable type of computing device as enumerated above. For instance, the compressive sensing sensors 302 may be used to detect motion or other activity of a user, and may be mounted on the body of the user or may be incorporated into an activity tracking device worn by the user anywhere on his body. The compressed sensing data may be transmitted wirelessly from the sensors 302 to the smartphone or smartwatch 310. In some examples, the smartphone 310 may include one or more applications to enable the user to view his or her sensed activity, vital signs, and the like. In such a case, the smartphone 310 may perform reconstruction and presentation of the received compressed sensing data. Additionally, or alternatively, the smartphone 310 may transmit the compressed sensing data and or the reconstructed data to a remote computing device 312 over the one or more networks 126, such as to a cloud server, web server, cloud-based storage device, or the like. Accordingly either or both of the computing devices 310 and 312 may correspond to the computing device 122 discussed above with respect to FIG. 1 and may perform the functions described with respect thereto. In some examples, the compressed sensing data may be transmitted to the remote computing device 312 over the one or more networks 126, the compressed sensing data may be processed by the computing device 122, and the resulting information may be transmitted back to the smartphone 310 for presentation to the user.

Some signals which are known to be sparse include fitness monitoring (via accelerometer, compass, gyrometer), ECG (via proximity sensors) etc. however implementations herein are not limited to these particular types of sensors described in the examples, and may be extended to various other types of sensors as will be apparent to those of skill in the art having the benefit of the disclosure herein. The activity signals are typically sparse in the frequency domain. For instance, a person jogging will have his or her foot hit the ground at a periodic/semi-periodic rate. Therefore, the post-processor in this case can use a wavelet transformation based CS system. Wavelet transformation can be DCT (discrete cosine transform), FFT (fast Fourier transform) or any other such matrix.

Figure 4:
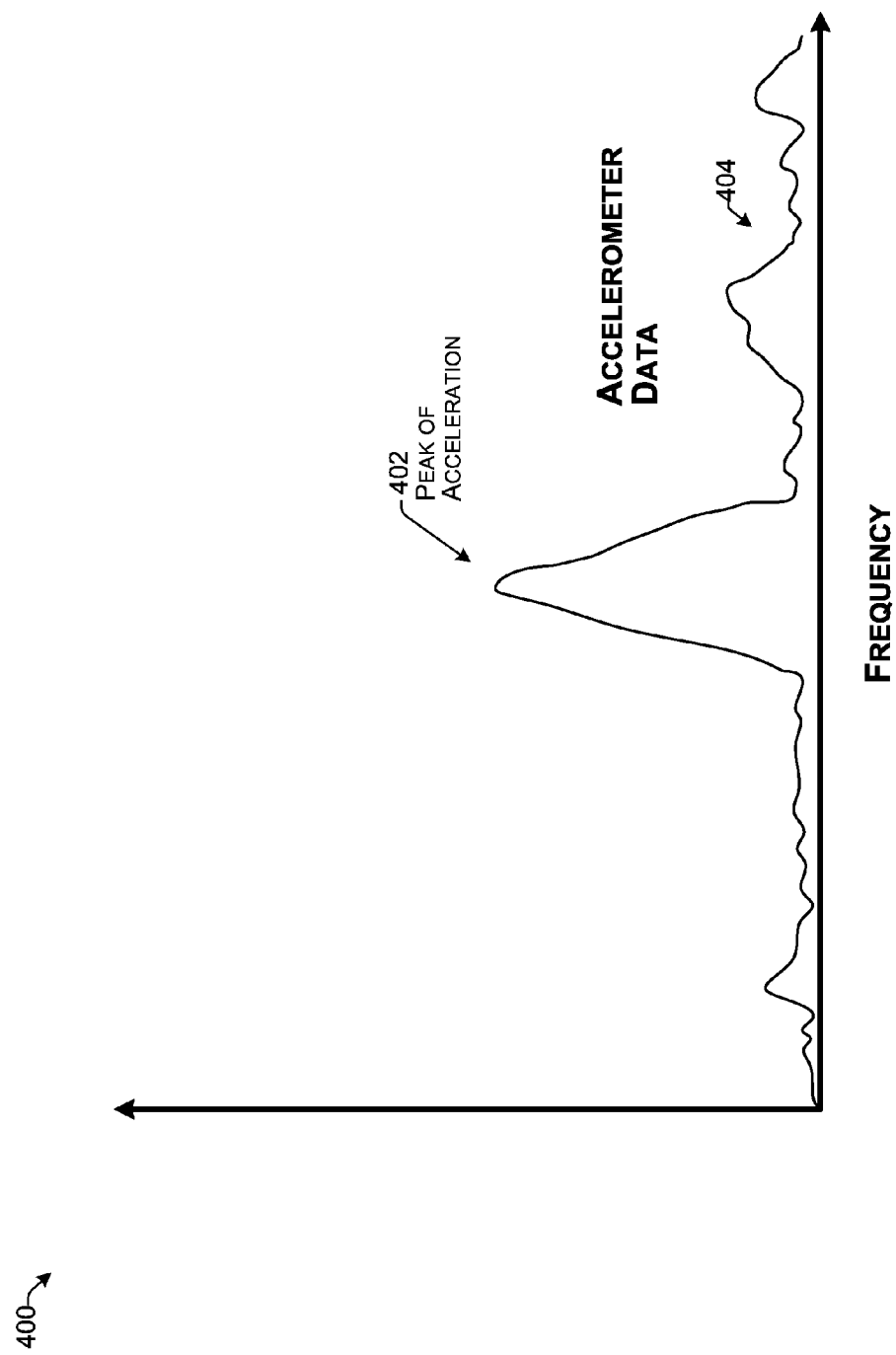
FIG. 4 illustrates an example of accelerometer data in the frequency domain according to some implementations.

FIG. 4 illustrates an example graph 400 illustrating accelerometer data as a function of frequency according to some implementations. This example shows an example of the accelerometer data in the frequency domain. The peak acceleration detected by the accelerometer is indicated at 402. As is evident the signal is extremely sparse. Noise is indicated at 404, and this noise may be removed by active thresholding.

Figure 5:
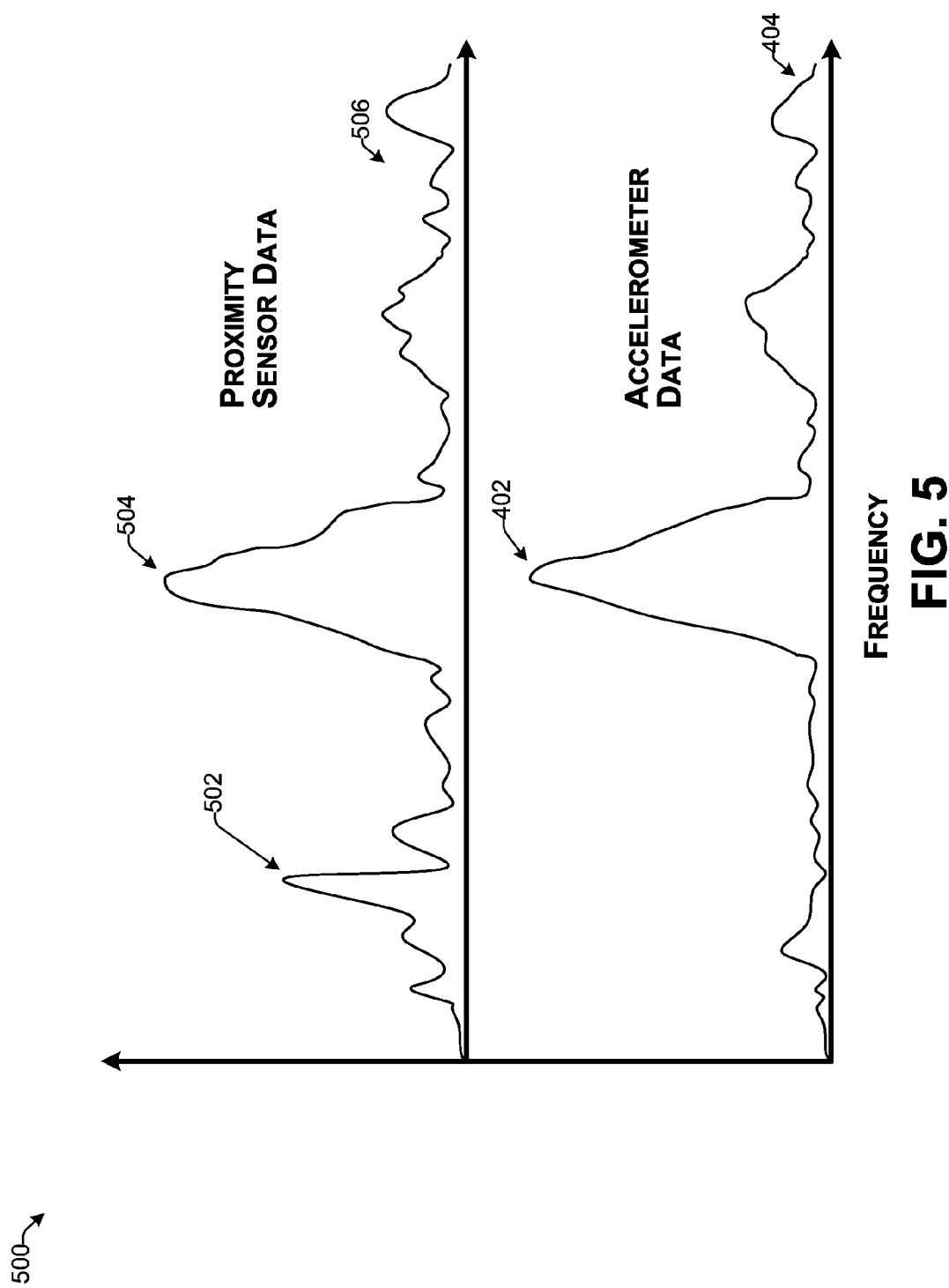
FIG. 5 illustrates an example of accelerometer data and proximity sensor data according to some implementations.

FIG. 5 illustrates an example graph 500 illustrating accelerometer data as a function of frequency along with corresponding proximity sensor data according to some implementations. In this example, the proximity sensor data indicates peaks at 502 and 504, and noise at 506. For instance, the proximity sensor may provide an indication of a person's heartbeat and the accelerometer sensor may provide an indication of the person's movement on the same time scale. A simple subtraction of the two may provide the actual heartbeat of the person. Consequently, by using a combination of various compressed activity monitor signals it is possible to apply intelligent algorithms to distinguish one activity from another with high degree of confidence.

Figure 6:
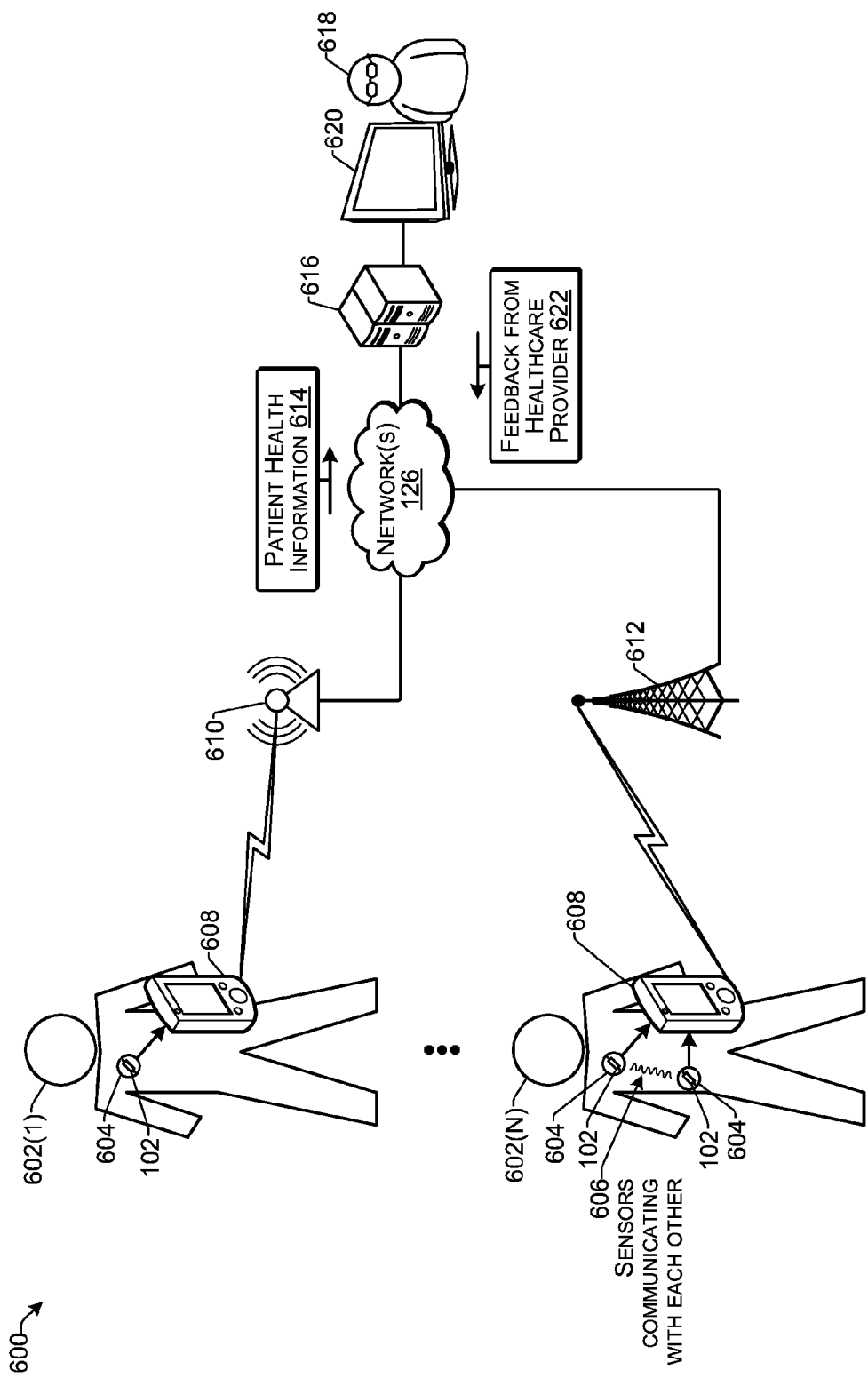
FIG. 6 illustrates an example of compressed sensor remote patient monitoring according to some implementations.

FIG. 6 illustrates another example system 600 that may employ compressed sensing according to some implementations herein. In this example, a plurality of users 602(1)-602(N) may each have one or more bodily mounted compressive sensing sensors 604, each of which may incorporate or may be connected to a sensor block 102, as discussed above. Furthermore, in some examples, when multiple sensors 604 are present on a user 602, as indicated at 606, the sensors 604 may be able to communicate with each other wirelessly in addition to sending compressed sensing data to a local computing device 608, such as smartphone, tablet computing device, mobile monitoring device, smartwatch or the like.

In this example, the sensor block 102 is applied to body area networks. The compressed sensing data is transmitted from any number of sensor blocks 102 to the local computing device 608. As several examples, the sensors 604 may comprise EEG (electroencephalography) electrodes for obtaining electrical data from a human patient's scalp, ECG (electrocardiography) electrodes for obtaining electrical data from a human patient's heart, CTG (cardiotocography) electrodes for obtaining electrical data from human patient's uterine contractions and/or fetal heartbeat, or other physical sensors for obtaining other medical or biological data from a human patient.

Furthermore, the local computing devices 608 may communicate with various network devices such as a wireless access point 610 and/or a cell tower 612 for transmitting patient health information 614 over the one or more networks 126 to a remote computing device 616. The compressed sensing data may be transmitted from the local computing device 608 to the remote computing device 616 as the compressed sensing data is received from the sensors 604, or may be transmitted periodically, such as when a threshold amount of compressed sensing data has been received.

The computing device 616 may be a cloud-based computing device that may employ an application including a reconstruction algorithm and that may also perform feature extraction to provide relevant data, such as for presentation to a healthcare professional 618 on a display 620. Based on the patient health information 614, the healthcare professional 618 or the computing device 616 may provide feedback 622 to one or more of the users 602. Furthermore, in some examples, the reconstruction may take place on the local computing device 608. Accordingly, either the local computing device 608 and/or the remote computing device 610 may correspond to the computing device 122 discussed above with respect to FIG. 1, and may perform the functions described with respect thereto.

Figure 7:
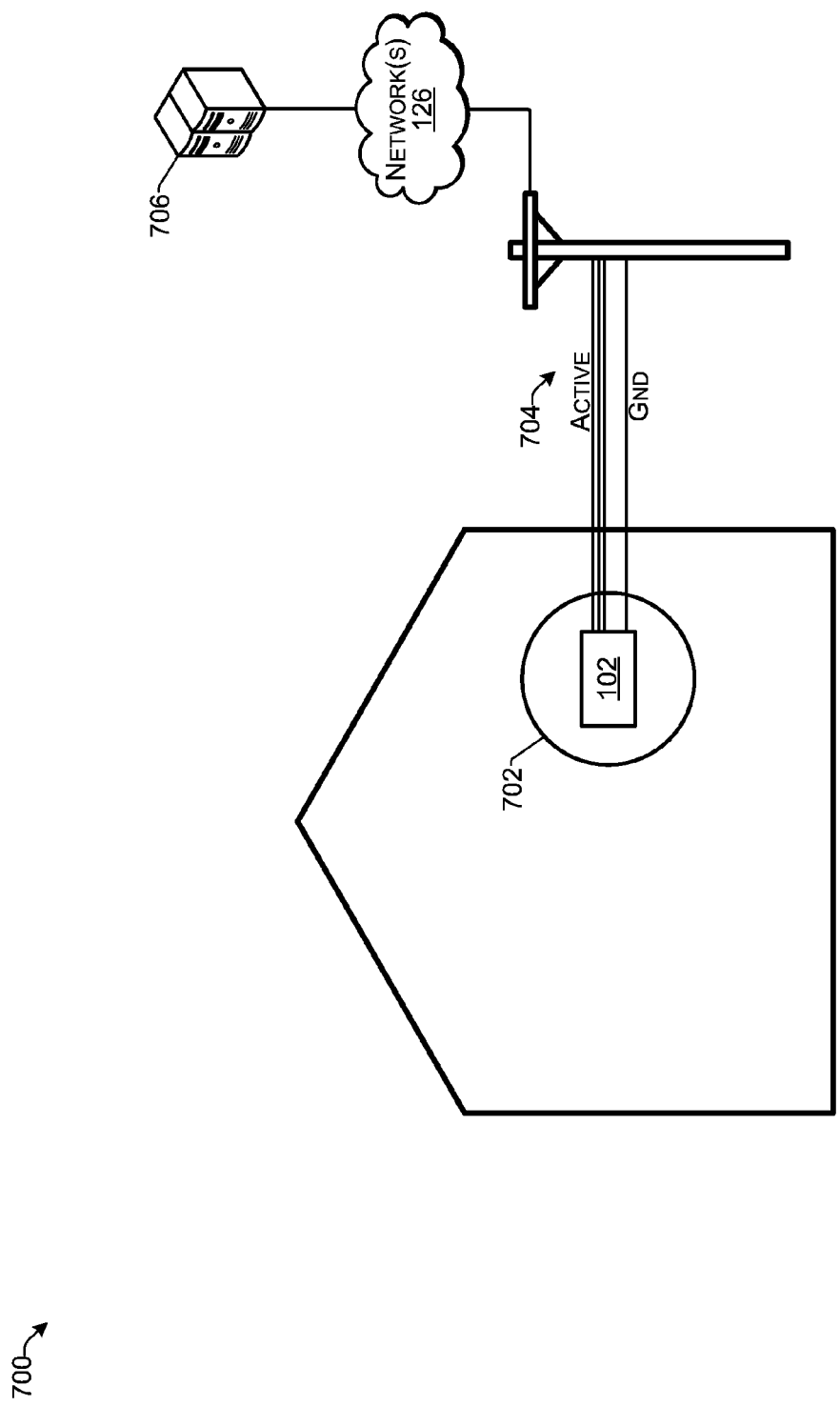
FIG. 7 illustrates an example of wired compressed sensor monitoring according to some implementations.

FIG. 7 illustrates an example system 700 for performing compressed sensing according to some implementations. In this example, a compressed sensing sensors 702 may include the sensor block 102 discussed above with respect to FIG. 1. In this example, the communication interface of the sensor block 102 may be configured to communicate over a hardwired connection through one or more wires 704 with the one or more networks 126, such as for sending compressed sensing data to a remote computing device 706. Accordingly, the remote computing device 706 may correspond to the computing device 122 discussed above with respect to FIG. 1, and may perform the functions described with respect thereto. Accordingly, there is nothing limiting the sensor systems herein to employ only a wireless network. The communication interface on the sensor block can be configured to send data over, a wire, cable, fiber optic, or the like, as well. In this case, the speed of transmission of the compressed sensing data may be reduced which may provide an added benefit.

Figure 8:
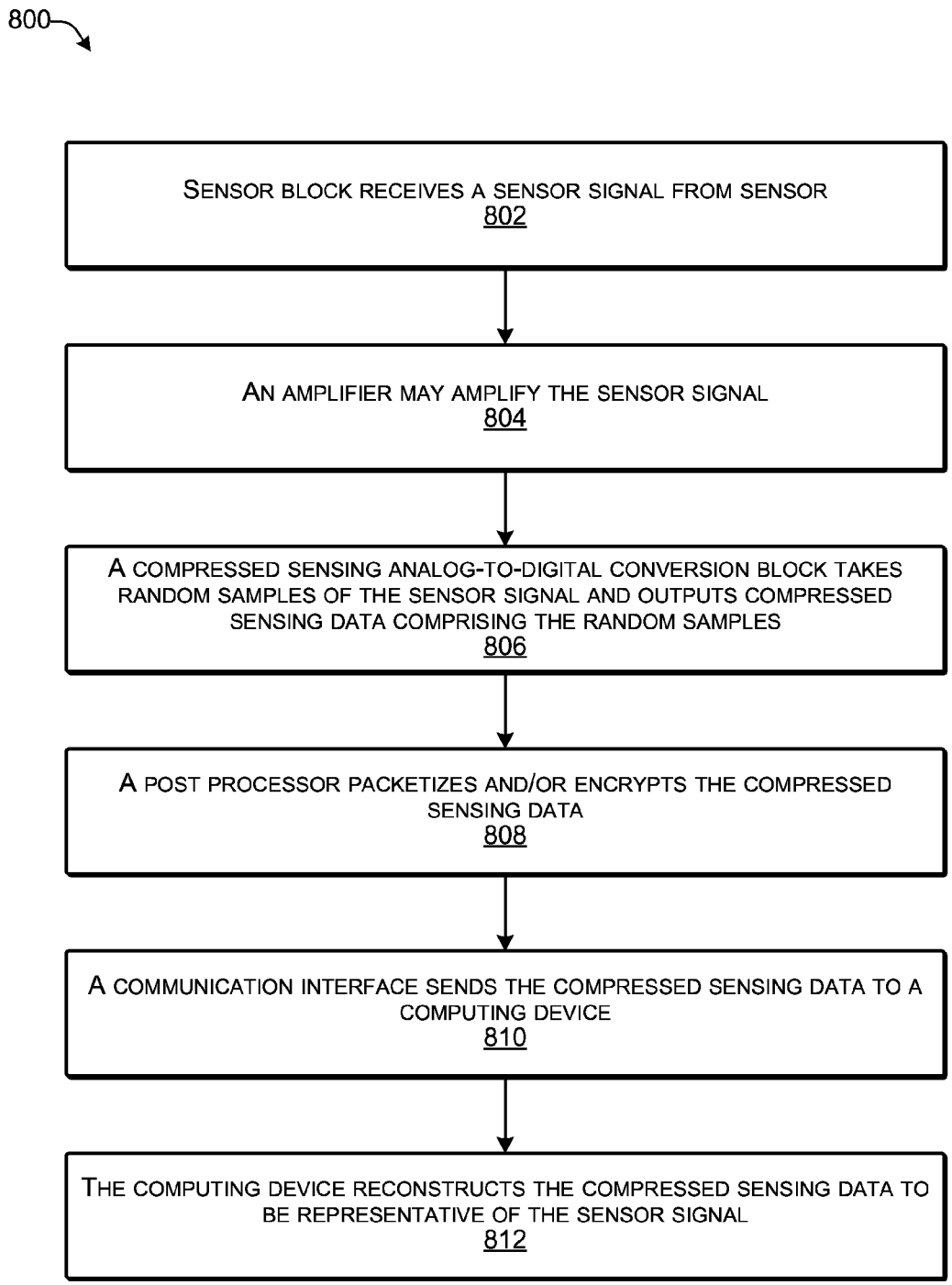
FIG. 8 is a flow diagram illustrating an example process according to some implementations.

FIG. 8 is a flow diagram illustrating example process 800 for compressed sensing according to some implementations. The process is illustrated as a collection of blocks in a logical flow diagram, which represents a sequence of operations, some or all of which can be implemented in hardware, software or a combination thereof. In the context of software, the blocks may represent computer-executable instructions stored on one or more computer-readable media that, when executed by one or more processors, program the processors to perform the recited operations. Generally, computer-executable instructions include routines, programs, objects, components, data structures and the like that perform particular functions or implement particular data types. The order in which the blocks are described should not be construed as a limitation. Any number of the described blocks can be combined in any order and/or in parallel to implement the process, or alternative processes, and not all of the blocks need be executed. For discussion purposes, the process is described with reference to the environments, architectures and systems described in the examples herein, although the process may be implemented in a wide variety of other environments, architectures and systems. In some examples, the process 800 may be executed at least in part by the sensor block 102.

At 802, the sensor block receives a sensor signal, such as from a sensor. For instance, the sensor signal may be a sparse signal.

At 804, an amplifier may amplify the sensor signal in some examples.

At 806, a compressed sensing ADC block takes random samples of the sensor signal and outputs compressed sensing data comprising the random samples. As an example, the compressed sensing ADC block may use a random number generator serving as a multiplication matrix for performing the random sampling, wherein a computing device that receives the compressed sensing data uses a corresponding random number generator and a decompression engine for decoding the compressed sensing data At 808, a post processor packetizes and/or encrypts the compressed sensing data.

At 810, a communication interface sends the compressed sensing data to at least one of a local or remote computing device.

At 812, the computing device reconstructs the compressed sensing data to be representative of the sensor signal.

The example processes described herein are only examples of processes provided for discussion purposes. Numerous other variations will be apparent to those of skill in the art in light of the disclosure herein. Further, while the disclosure herein sets forth several examples of suitable frameworks, architectures and environments for executing the processes, implementations herein are not limited to the particular examples shown and discussed. Furthermore, this disclosure provides various example implementations, as described and as illustrated in the drawings. However, this disclosure is not limited to the implementations described and illustrated herein, but can extend to other implementations, as would be known or as would become known to those skilled in the art.

Figure 9:
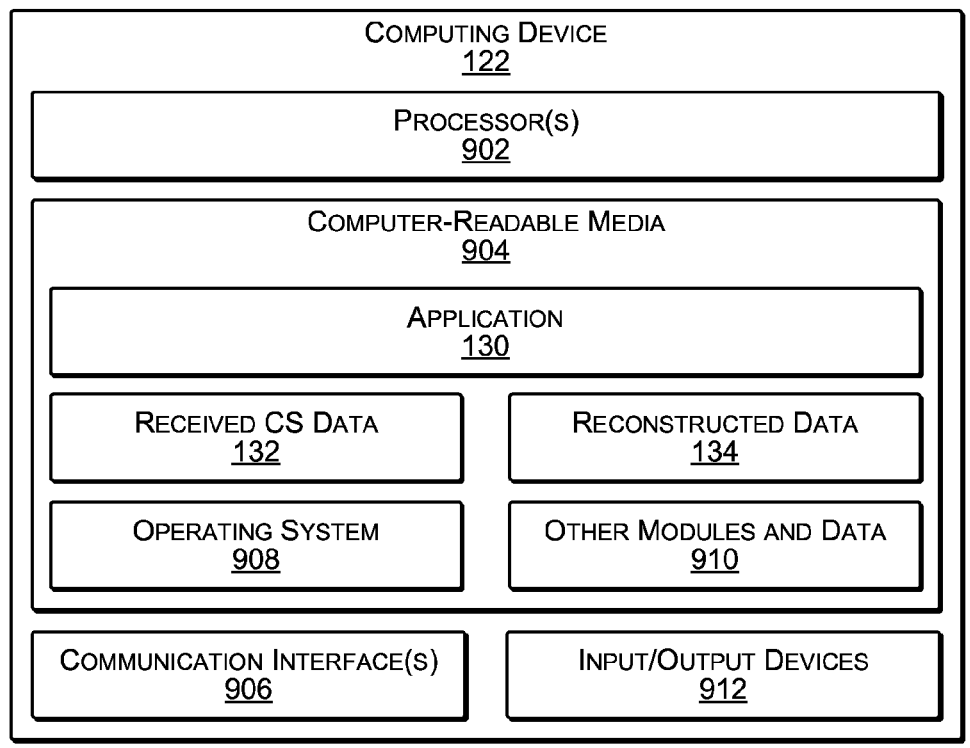
FIG. 9 illustrates select components of one or more example computing devices according to some implementations.

FIG. 9 illustrates select components of the computing device 122 that may be used to implement some functionality of the compressed sensing data storage and/or processing described herein. In some examples, the computing device 122 may be operated by a service provider, and may include one or more servers or other types of computing devices that may be embodied in any number of ways. For instance, in the case of a server, the application, other functional components, and data storage may be implemented on a single server, a cluster of servers, a server farm or data center, a cloud-hosted computing service, a cloud-hosted storage service, and so forth, although other computer architectures may additionally or alternatively be used. Alternatively, in the case of a local computing device 122, the computing device 122 may be a desktop computer, laptop computer, tablet computer, workstation, mobile device, cellphone, smartphone, smartwatch, wearable computing device, or any other computing device having sufficient storage and processing capabilities to perform the functions discussed above.

In the illustrated example, the computing device 122 may include, or may have associated therewith, one or more processors 902, one or more computer-readable media 904, and one or more communication interfaces 906. Each processor 902 may be a single processing unit or a number of processing units, and may include single or multiple computing units or multiple processing cores. The processor(s) 902 can be implemented as one or more microprocessors, microcomputers, microcontrollers, digital signal processors, central processing units, state machines, logic circuitries, and/or any devices that manipulate signals based on operational instructions. For instance, the processor(s) 902 may be one or more hardware processors and/or logic circuits of any suitable type specifically programmed or configured to execute the algorithms and processes described herein. The processor(s) 902 can be configured to fetch and execute computer-readable instructions stored in the computer-readable media 904, which can program the processor(s) 902 to perform the functions described herein.

The computer-readable media 904 may include volatile and nonvolatile memory and/or removable and non-removable media implemented in any type of technology for storage of information, such as computer-readable instructions, data structures, program modules, or other data. Such computer-readable media 904 may include, but is not limited to, RAM, ROM, EEPROM, flash memory or other memory technology, optical storage, solid state storage, magnetic tape, magnetic disk storage, RAID storage systems, storage arrays, network attached storage, storage area networks, cloud storage, or any other medium that can be used to store the desired information and that can be accessed by a computing device. Depending on the configuration of the computing device 122, the computer-readable media 904 may be a type of computer-readable storage media and/or may be a tangible non-transitory media to the extent that when mentioned, non-transitory computer-readable media exclude media such as energy, carrier signals, electromagnetic waves, and signals per se.

The computer-readable media 904 may be used to store any number of functional components that are executable by the processors 902. In many implementations, these functional components comprise instructions or programs that are executable by the processors 902 and that, when executed, specifically configure the one or more processors 902 to perform the actions attributed above to the computing device 122. Functional components stored in the computer-readable media 904 may include the application 130. Additional functional components stored in the computer-readable media 904 may include an operating system 908 for controlling and managing various functions of the computing device 122.

In addition, the computer-readable media 904 may store data used for performing the functions and services described herein. Thus, in some examples, the computer-readable media 904 may store the received compressive sensing data 132, and the reconstructed data 134. The computing device 122 may also include or maintain other functional components and data, such as other modules and data 910, which may include programs, drivers, etc., and the data used or generated by the functional components. Further, the computing device 122 may include many other logical, programmatic, and physical components, of which those described above are merely examples that are related to the discussion herein.

The communication interface(s) 906 may include one or more interfaces and hardware components for enabling communication with various other devices, such as over the network(s) 132. For example, communication interface(s) 906 may enable communication through one or more of the Internet, cable networks, cellular networks, wireless networks (e.g., Wi-Fi) and wired networks, as well as close-range communications such as BLUETOOTH®, and the like, as additionally enumerated elsewhere herein. Additionally, in some examples, the computing device 122 may be directly connect to the sensor blocks herein over hardwired connections, pluggable connections, optical communication interfaces, and the like, as additionally enumerated herein.

The computing device 122 may further be equipped with various input/output (I/O) devices 912. Such I/O devices 912 may include a display, various user interface controls (e.g., buttons, joystick, keyboard, mouse, touch screen, etc.), microphone, audio speakers, connection ports and so forth.

Various instructions, methods, and techniques described herein may be considered in the general context of computer-executable instructions, such as program modules stored on computer-readable media, and executed by the processor(s) herein. Generally, program modules include routines, programs, objects, components, data structures, etc., for performing particular tasks or implementing particular abstract data types. These program modules, and the like, may be executed as native code or may be downloaded and executed, such as in a virtual machine or other just-in-time compilation execution environment. Typically, the functionality of the program modules may be combined or distributed as desired in various implementations. An implementation of these modules and techniques may be stored on computer storage media or transmitted across some form of communication media.

Although the subject matter has been described in language specific to structural features and/or methodological acts, it is to be understood that the subject matter defined in the appended claims is not necessarily limited to the specific features or acts described. Rather, the specific features and acts are disclosed as example forms of implementing the claims.

What is claimed is:

1. A sensor block comprising:
   an amplifier to receive a sensor signal from a sensor and output an amplified signal;
   a compressed sensing analog-to-digital conversion block coupled to the amplifier, the compressed sensing analog-to-digital conversion block including a random number generator that generates random values to enable an analog-to-digital converter (ADC) to take random samples of the amplified signal based on the random values, and output compressed sensing data comprising the random samples;
a post processor coupled to the compressed sensing analog-to-digital conversion block to receive the compressed sensing data and remove noise from the compressed sensing data by active thresholding; and
a communication interface coupled to the post processor to receive the compressed sensing data from the post processor and send the compressed sensing data to a computing device, wherein the sensor block further utilizes the random number generator for encrypting the compressed sensing data prior to sending to the computing device.

2. The sensor block as recited in claim 1, wherein the ADC takes the random samples converting the amplified signal from an analog signal to a digital signal based on the random values generated by the random number generator to generate a sparse random sampling of the amplified signal.

3. The sensor block as recited in claim 1, wherein:
the random number generator is a linear feedback shift register; and
the ADC is a switched capacitor ADC.

4. The sensor block as recited in claim 1, wherein the sensor block further utilizes the random number generator for encrypting the compressed sensing data prior to sending to the computing device by using the random number generator to generate a randomization matrix for encrypting the compressed sensing data, wherein the computing device is able to read the encrypted compressed sensing data using a corresponding randomization matrix.

5. The sensor block as recited in claim 1, wherein the communication interface comprises a transmitter and an antenna for wirelessly transmitting the compressed sensing data to the computing device.

6. The sensor block as recited in claim 1, wherein the communication interface comprises a wired connection for transmitting the compressed sensing data to the computing device.

7. The sensor block as recited in claim 1, wherein the sensor block is associated with an activity monitor and is integrated with at least one of:
an accelerometer;
a gyrometer;
a compass;
a proximity sensor;
electrocardiogram sensor;
a heart rate monitor;
a pressure sensor; or
a GPS receiver.

8. The sensor block as recited in claim 1, further comprising a storage for receiving the compressed sensing data prior to sending to the computing device, wherein at least one of the storage, the post-processor, or the communication interface cycle between an active state and a quiescent state based at least in part on at least one of:
an occurrence of sampling of the sensor signal by the compressed sensing analog-to-digital conversion block;
an amount of compressed sensing data stored in the storage reaching a threshold amount; or
an input from the user.

9. The sensor block as recited in claim 1, wherein at least the compressed sensing analog-to-digital conversion block and the post processor are incorporated into an application-specific integrated circuit.

10. The sensor block as recited in claim 1, wherein the computing device is programmed to at least one of:
reconstruct the compressed sensing data to generate a representation of the sensor signal;
perform predictive analytics on the reconstructed compressed sensing data; or
provide access of third party tools to the compressed sensing data.

11. The sensor block as recited in claim 1, wherein the sensor block is incorporated into a wearable device comprising at least one of:
an activity monitor;
an electrocardiogram monitor;
an audio receiver;
a smartwatch or bracelet; or
a media player.

12. A system for collecting and processing sensor data, the system comprising:
a sensor block comprising:
a compressed sensing analog-to-digital conversion block to receive a sensor signal, the compressed sensing analog-to-digital conversion block including a random number generator that causes a circuit to take random samples of the sensor signal based on randomly generated values from the random number generator and output compressed sensing data comprising the random samples;
a post processor coupled to the compressed sensing analog-to-digital conversion block to receive the compressed sensing data and remove noise from the compressed sensing data by active thresholding; and
a communication interface coupled to the post processor to receive the compressed sensing data from the post processor and send the compressed sensing data to a computing device, wherein the sensor block further utilizes the random number generator for encrypting the compressed sensing data prior to sending to the computing device.

13. The system as recited in claim 12, further comprising the computing device, wherein the computing device is programmed to:
receive the compressed sensing data; and
reconstruct the compressed sensing data to generate a representation of the sensor signal.

14. The system as recited in claim 12, further comprising an amplifier to receive the sensor signal from a sensor and amplify the sensor signal provided to the compressed sensing analog-to-digital conversion block.

15. The system as recited in claim 12, wherein the compressed sensing analog-to-digital conversion block comprises an analog-to-digital converter (ADC), wherein the ADC takes the random samples by converting the sensor signal from an analog signal to a digital signal based on the random values generated by the random number generator to generate a sparse random sampling of the sensor signal.

16. The system as recited in claim 12, wherein the sensor signal received from the sensor is a sparse signal in the frequency domain.

17. The system as recited in claim 12, wherein the sensor signal received from the sensor is a sparse signal in a time domain.

18. A method of collecting and processing sensor data, the method comprising:

obtaining a sensor signal from a sensor carried by a person;

generating compressed sensing data using a compressed sensing analog-to-digital conversion block that uses values generated by a random number generator for taking random samples of the sensor signal at a frequency below a Nyquist rate;

processing the compressed sensing data using a post processor to remove noise from the compressed sensing data by active thresholding, utilize the random number generator to encrypt the compressed sensing data, and packetize the encrypted compressed sensing data; and sending the packetized encrypted compressed sensing data to a computing device over a wireless connection.

19. The method as recited in claim 18, wherein:

the sensor is integrated with the compressed sensing analog-to-digital conversion block;

the sensor is associated with an activity monitor; and the sensor comprises at least one of:
   an accelerometer;
   a gyrometer;
   a compass;
   a proximity sensor;
   electrocardiogram sensor;
   a heart rate monitor;
   a pressure sensor; or
   a GPS receiver.

20. The method as recited in claim 18, wherein generating the compressed sensing data using a compressed sensing analog-to-digital conversion block comprises using the random number generator and an analog-to-digital converter (ADC), wherein the ADC takes the random samples by converting the sensor signal from an analog signal to a digital signal based on the random values generated by the random number generator to generate a sparse random sampling of the sensor signal.

21. The method as recited in claim 18, wherein the computing device receives the packetized encrypted compressed sensing data and uses a corresponding random number generator for decoding the packetized encrypted compressed sensing data.

22. The method as recited in claim 18, further comprising using wavelet transforms to enable compressed sensing on one or more activity sensors incorporating one or more respective compressed sensing analog-to-digital conversion blocks.

* * * * *